United States Patent
Ferko, IV

(10) Patent No.: US 7,033,601 B1
(45) Date of Patent: Apr. 25, 2006

(54) COMPOSITION AND METHOD FOR REPELLING SQUAMATE REPTILES

(75) Inventor: George Ferko, IV, Palmerton, PA (US)

(73) Assignee: Liquid Holding Company, Inc., Brodheadsville, PA (US)

( * ) Notice: Subject to any disclaimer, the term of this patent is extended or adjusted under 35 U.S.C. 154(b) by 0 days.

(21) Appl. No.: 11/125,677

(22) Filed: May 10, 2005

(51) Int. Cl.
*A01N 25/00* (2006.01)

(52) U.S. Cl. .................. 424/405; 106/15.05; 424/581; 424/725; 424/747; 424/754

(58) Field of Classification Search ............. 106/15.05; 424/405, 581, 725, 747, 754
See application file for complete search history.

(56) References Cited

U.S. PATENT DOCUMENTS

| | | | | |
|---|---|---|---|---|
| 3,069,314 | A * | 12/1962 | Jenkins | 424/40 |
| 5,356,881 | A * | 10/1994 | Verbiscar | 514/26 |
| 5,698,191 | A * | 12/1997 | Wiersma et al. | 424/78.09 |
| 5,993,891 | A * | 11/1999 | Danielson et al. | 427/4 |
| 6,231,865 | B1 * | 5/2001 | Hsu et al. | 424/739 |
| 6,244,518 | B1 * | 6/2001 | Pogue | 239/36 |
| 6,248,364 | B1 * | 6/2001 | Sengupta et al. | 424/501 |
| 6,375,968 | B1 * | 4/2002 | Quong | 424/408 |
| 6,689,397 | B1 * | 2/2004 | Clark et al. | 424/725 |

FOREIGN PATENT DOCUMENTS

| | | |
|---|---|---|
| CN | 1123602 | 6/1996 |
| JP | 9-110623 A * | 4/1997 |

OTHER PUBLICATIONS

Putrescent Whole Egg Solids-Pesticide Fact Sheet, http://web.archive.org/web/19961231223601/www.infoventures.com/e-hlth/pesticide/bgr2.htm (Dec. 31, 1996).*

Chiszar, D., et al., "Stimulus Control of Predatory Attack in the Brown Tree Snake(*Boiga irregularis*). 2. Use of chemical cues during foraging", Amphibia-Reptilia, vol. 9 (1988), pp. 77-88, (no month).

Chiszar, D., et al., "Experiments on Chemical Control of Behavior in Brown Tree Snakes", Repellants in Wildlife Management, National Wildlife Research Center, Fort Collins, CO, JR Mason Editor, (1997), pp. 121-127, (no month).

Chiszar, D., Chemical Control of Predatory Behavior in the Brown Tree Snake (*Bioga irregularis*), vol. 24, (1992), p. 108, (no month).

Chiszar, D., et al., "Stimulus Control of Predatory Attack in the Brown Tree Snake (*Bioga irregularis*). 1. Effects of Visual Cues Arising From Prey", The Snake, vol. 20, (1998), pp. 151-155, (no month).

http://www.aphis.usda.gov/lpa/pubs/tn_wmsnakerepellent.html. "Snake Repellents", (Mar. 25, 2005), published Apr. 2003 by the USDA.

* cited by examiner

*Primary Examiner*—Anthony J. Green
(74) *Attorney, Agent, or Firm*—Maryellen Feehery; Reed Smith LLP

(57) ABSTRACT

The present invention is a composition and method for repelling squamate reptiles, such as without limitation snakes. The composition comprises mint oil, garlic oil, putrescent egg solids, thyme oil white, sodium lauryl sulfate and water. This composition is applied to snakes' habitats or perimeters around homes, buildings, patios, decks and the like to repel squamate reptiles, such as without limitation snakes.

17 Claims, No Drawings

COMPOSITION AND METHOD FOR REPELLING SQUAMATE REPTILES

BACKGROUND OF THE INVENTION

Snakes and other squamate reptiles inhabit and nest in areas which may be close to where humans live and spend time. Due to the danger of snake bites, venomous and not, and other bad associations with snakes, many homeowners and people engaging in recreational activities, such as camping, have tried to find ways to repel snakes from the vicinity of humans. Optimally, the repellent does not kill the snakes, but merely repels them from the human's vicinity.

Many prior art repellents are not effective at repelling snakes, or only repel the snakes for a short period of time. A more reliable repellent was desired.

It is believed that squamate reptiles, in particular snakes, rely on three separate chemosensory systems for much of their environmental information. The taste buds (or gustatory system) gathers information from the materials in the saliva. Second, the olfactory sensors detect volatile, low molecular weight chemicals. Third, the vomeronasal system is sensitive to high molecular weight molecules, primarily via the vomeronasal organ. The vomeronasal organ in a snake opens into the roof of the mouth, and snakes use the tip of the tongue to deliver environmental chemicals to the organ.

Squamate reptiles, such as without limitation lizards and snakes, pick up vomodors (usually heavy compounds that settle on substrates or are in the air) from substrates and the air by tongue flicking. In snakes and Scleroglossan lizards, the tongue is specialized, used only for vomodor gathering. The present invention, without being limited to mechanism, recognizes the usefulness of vomodors in snake repellents.

SUMMARY OF THE INVENTION

According to the present invention, a composition comprising garlic oil, putrescent egg solids and one or more of: camphor; camphene; menthol; menthene; carvacrol: thymol: carvone: 1,8-cineol (also known as cajuputol or eucalyptol); compositions containing one or more of camphor, camphene, menthol, menthene, carvacrol, thymol, carvone, and 1,8-cineol (see Table 2 for preferable concentration ranges) ("Sources"); and mixtures thereof, are effective snake repellents. The composition may be in a liquid form, which in one embodiment, can be concentrated and then diluted with water before use (e.g. without limitation with a hose sprayer). Preferably, the composition to water ratio is about 1:8 v/v to about 1:18 v/v, when it is applied. In another embodiment, the composition may be on or part of a solid, preferably a granular solid, which may be deposited in the desired areas.

The composition may be applied liberally on and around outside areas that squamate reptiles, such as without limitation snakes, have inhabited and/or nested. This includes, but is not limited to, snakes' nests, shelters, rocks, grass, dirt, trees, roots, shrubs, plants and buildings/man-made structures. It is preferred without limitation that the composition is applied during a dry period.

In another embodiment, the composition may be applied in about a 2–3 foot wide band around the perimeter of an outside area that it is desired to protect from squamate reptiles, such as without limitation snakes. In one embodiment, the composition is reapplied every 2–3 weeks. If above average rainfall occurs, the composition may be reapplied.

The present invention repels squamate reptiles, such as without limitation snakes, without harming or killing them and without affecting the surrounding plant life or damaging the buildings or surfaces upon which the composition is deposited.

DETAILED DESCRIPTION OF THE INVENTION

The present invention uses naturally odiferous chemical compounds that have been known to produce deterrents or repellents for other animals, mixed together to produce a mixture that will repel squamate reptiles, such as without limitation snakes, particularly snakes common to the U.S.

One embodiment of the repellent composition follows:

TABLE 1

| Component | Manufacturer | % Concentrate | % Ready to Use |
|---|---|---|---|
| Mint Oil | Polarome | 25.04 | 3.13 |
| Garlic Oil | Polarome | 6.24 | 0.78 |
| Putrescent Egg Solid | Inovatech | 6.24 | 0.78 |
| Thyme Oil White | Polarome | 9.36 | 1.17 |
| Sodium Lauryl Sulfate | Univar | 9.36 | 1.17 |
| Water | Nesquehoning | 43.76 | 92.97 |

All percentages given in this specification are given as weight percentages, unless otherwise noted.

The composition of the present invention may be prepared as a concentrate and then administered via a hose spray, or mixed with water in another manner. Additionally, it may be prepared as "ready to use" with the sufficient quantity of water to allow spreading, but not too much to dilute the amounts of garlic oil, putrescent egg solids and one or more of: menthol, menthene, camphor, camphene, carvacrol, thymol, carvone or 1,8-cineol so that the squamate reptiles, such as without limitation snakes, do not detect the repellent in the vomeronasal organ, or detect and ignore the repellent. The preferred ranges for these components are set forth in Table 2.

TABLE 2

| Component | Concentrate Preferred % Ranges | Ready To Use Preferred % Ranges |
|---|---|---|
| Menthol | about 4% to about 50.4% | about 0.5% to about 4.2% |
| Menthene | about 2.4% to about 8.9% | about 0.3% to about 0.7% |
| Camphor | about 1.6% to about 13.8% | about 0.2% to about 1.2% |
| Camphene | about 1.6% to about 16.8% | about 0.2% to about 1.4% |
| 1,8-Cineol | about 9.6% to about 22.8% | about 1.2% to about 1.9% |
| Carvone | about 4.8% to about 40.8% | about 0.6% to about 3.4% |
| Carvacrol | about 4% to about 30% | about 0.5% to about 2.5% |
| Thymol | about 4.0% to about 38.4% | about 0.5% to about 3.2% |

Additionally, the compositions may be prepared as liquids which are then deposited on solids, e.g. without limitation particulates, granules, crushed egg shells, sawdust, diatomaceous earth, dried kelp, and fuller's earth. It is preferred that the solids are fine because they are easier to disperse in the barriers or snakes' habitats.

Other embodiments of the present invention include: garlic oil, putrescent egg solids and one or more of compositions containing high levels of menthol, menthene, camphor, camphene, carvacrol, thymol, carvone or 1,8-cineol.

Compositions containing high levels of menthol and/or menthene include but are not limited to cornmint oil, spearmint oil, horsemint oil, round leaf mint oil, oil of hyssop, Japanese mint oil, European pennyroyal, and American pennyroyal.

Compositions containing high levels of camphor, camphene and/or 1,8-cineol include but are not limited to tea tree oil, cardamon oil, red thyme oil (thymus vulgaris), white thyme oil (thymus zygis), Spanish marjoram oil (thymus mantichina), rosemary oil and sage oil.

Other embodiments include garlic oil, putrescent egg solids, and mint oils. The preferred mint oil have either high levels (either individually or net) of one or more of: menthol, menthene, camphor, camphene, carvacrol, thymol, carvone and 1,8-cineol.

In some embodiments, surfactants, preferably without limitation alkyl sulfates, more preferably sodium lauryl sulfates, may be used to maintain homogeneity of the composition. Weaker surfactants will need to be present in higher amounts than stronger surfactants, such as sodium lauryl sulfates.

In some embodiments, it may be desirable to add additional components to the compositions, such as plant fertilizers, plant growth stimulants, repellents for other animals, repellents for insects, colorants, preservatives, dyes, and perfumes.

It is believed without being limited to mechanism, that the composition repels snake due to the exposure of the composition and its components to the snake's tongue and vomeronasal organ. The following study shows that snakes were repelled from the composition set forth in Table 1.

EXAMPLE 1

Fifty-one (51) snakes were tested for their response to the formulation set forth in Table 1. Most of the snakes were members of the family Colubridae. The snakes and how they were acquired are set forth in Table 2.

TABLE 2

| Species | Common Name | Number | Origin |
|---|---|---|---|
| Diadophis punctatus edwardsi | Northern ringneck snake | 1 | W |
| Heterodon platirhinos | Eastern hognose snake | 1 | W |
| Liochlorophis vernalis | Smooth green snake | 3 | W |
| Elaphe guttata | Corn snake | 3 | L |
| Elaphe obsoleta spilotes | Gray ratsnake | 4 | P |
| Elaphe obsoleta quadrivittata | Yellow ratsnake | 3 | P,L |
| Elaphe obsoleta rossalleni | Everglades ratsnake | 2 | P |
| Lampropeltis getula californiae | California kingsnake | 1 | L |
| Lampropeltis getula nigrita | Desert black kingsnake | 2 | P |
| Lampropeltis getula holbrooki | Speckled kingsnake | 3 | P |
| Lampropeltis triangulum campbelli | Pueblan milksnake | 2 | P |
| Lampropeltis t.' triangulum | Eastern milksnake | 2 | W |
| Pituophis catenifer sayi | Bullsnake | 4 | P |
| Pituophis m. melanoleucus | Northern pine snake | 1 | L |
| Nerodia s. sipedon | Northern watersnake | 1 | W |
| Storeria occipitomaculata | Red-bellied snake | 4 | W |

TABLE 2-continued

| Species | Common Name | Number | Origin |
|---|---|---|---|
| Thamnophis s. sirtalis | Eastern garter snake | 4 | W |
| Agkistrodon c. contortrix | Southern copperhead | 2 | P |
| Agkistrodon p. piscivorus | Eastern cottonmouth | 2 | P |
| Agkistrodon p. conanti | Florida cottonmouth | 1 | P |
| Crotalus atrox | W. Diamondback rattlesnake | 5 | P |

*L means long-term captive, P means purchased, and W means wild-caught.

The snakes were kept on a 14 hr. light/10 hr. dark schedule. Small snakes were fed twice weekly and large snakes were fed weekly. Water was available ad libidum. A few of the snakes did not survive the entire test prior for reasons apparently unrelated to the testing.

The testing occurred in wooden chambers 119 cm in internal length, 28 cm in internal width and 28 cm in internal height. The floor, back and sides were wood painted with an odorless paint, and the front was plexiglass, while the top was a screen in a wooden frame. The front of each chamber was marked in one centimeter intervals. The floors were lined with newspaper and 2 wooden shelters were placed at each end of the chamber (one at each end).

During the trial, a snake was placed in the center of the chamber and allowed to acclimate for 60 minutes. During some runs, a light was placed over one of the shelters to provide a source of heat. Snakes sometimes are attracted to heat. Controls were run with no repellent in the chambers. During the other trials, absorbent pads were placed in one shelter on top of duct tape (which was over the floor) at about the point designated 0 cm. At the end of the acclimation period, about 1.5 ml of the formulation was added to the absorbent pad. The snake's position was then recorded every ten minutes until fifteen positions were recorded.

The snakes behaved in three different ways. First, some snakes entered a coiled position and remained essentially motionless. Second, some snakes wandered about the chamber for the entire test. Third, some snakes intermittently moved gradually from one part of the chamber to another. All three behaviors were recorded in control trials and experimental trials. A few snakes escaped through cracks between the lid and wall, and were recaptured in time to be re-introduced to the chamber before the next positional reading.

Some snakes moved about frequently and showed no overt reaction to the repellent. However, other snakes did stop near the repellent, flicked their tongues and moved in a different direction, noticing the repellent.

The mean average position for each treatment produced the following mean of the snakes' average positions.

TABLE 3

| Mean Average Positions (cm) | Treatment Type |
|---|---|
| about 45 | light on, no repellent |
| about 55 | light off, no repellent |
| about 80 | light on, repellent |
| about 75 | light off, repellent |

The mean of the average positions of the snakes was tested using two way analysis of variance in order to separate the effects of heat and repellent. The repellent effects were highly significant, while the light effect was non-significant.

The repellent was present at about 0 cm, and from these results, it is apparent that the snakes preferred to stay away from the repellent. Based on these results, the formulation had a definite repellent effect.

There were some snakes that were restless in both the control and experimental trials. It is possible that this restlessness was caused by the motivation to escape, and that non-captive snakes would have a stronger tendency to avoid the repellent.

It is to be understood that while the invention has been described in conjunction with the detailed description thereof, that the foregoing description is intended to illustrate and not limit the scope of the invention, which is defined by the scope of the appended claims. Other aspects, advantages, and modifications are evident from a review of the following claims.

What is claimed is:

1. A squamate repellent composition comprising
    Mint oil at about 25%,
    Garlic oil at about 6%,
    Putrescent egg solids at about 6%,
    Thyme oil white at about 9%, and
    Sodium lauryl sulfate at about 9%.

2. A squamate repellent composition comprising mint oil, garlic oil putrescent egg solids, thyme oil white, and sodium lauryl sulfate.

3. A squamate mate repellent composition comprising garlic oil, putrescent egg solids, one or more surfactants, and one or more compounds selected from the group consisting of camphor, camphene, menthol, menthene, carvacrol, thymol, carvone, 1,8-cineol, Sources and mixtures thereof.

4. The composition of claim 3 wherein the surfactants are alkyl sulfates.

5. The composition of claim 3 wherein the composition is liquid.

6. The composition of claim 3 wherein the composition is solid.

7. The composition of claim 3 wherein the one or more compounds are selected from the group consisting of cornmint oil, spearmint oil, horsemint oil, roundleaf mint oil, oil of hyssop, Japanese mint oil, European pennyroyal and American pennyroyal.

8. The composition of claim 3 wherein the one or more compounds are selected from the group consisting of tea tree oil, cardamon oil, red thyme oil, white thyme oil, Spanish marjoram oil, rosemary oil and sage oil.

9. A method of repelling squamate reptiles comprising
    Applying a composition comprising mint oil garlic oil, putrescent egg solids, thyme oil white, and sodium lauryl sulfate to an area known to be inhabited by snakes.

10. A method of repelling squamate reptiles comprising
    Applying a composition comprising garlic oil, putrescent egg solids, one or more surfactants, and one or more compounds selected from the group consisting of camphor, camphene, menthol, menthene, 1,8-cineol, carvacrol, thymol, cavone, Sources and mixtures thereof to a perimeter of a protected region.

11. The method of claim 10 wherein the surfactants are alkyl sulfates.

12. The method of claim 10 wherein the squamate reptiles are snakes.

13. The method of claim 10 further comprising diluting the composition with water before the applying occurs.

14. The method of claim 10 wherein the composition is liquid.

15. The method of claim 10 wherein the composition is solid.

16. The method of claim 10 further comprising repeating the application about 2 weeks after the first application.

17. The method of claim 10 wherein the applying occurs during a dry period.

\* \* \* \* \*

UNITED STATES PATENT AND TRADEMARK OFFICE
CERTIFICATE OF CORRECTION

| | | |
|---|---|---|
| PATENT NO. | : 7,033,601 B1 | Page 1 of 1 |
| APPLICATION NO. | : 11/125677 | |
| DATED | : April 25, 2006 | |
| INVENTOR(S) | : George J. Ferko, IV | |

It is certified that error appears in the above-identified patent and that said Letters Patent is hereby corrected as shown below:

The Inventor's name, item (75) on the face of the patent, should read as --George J. Ferko, IV--

In Column 4, line 18, "ad libidum" should be in italics.

In Column 5, line 30, "mate" should be deleted.

Signed and Sealed this

Twenty-fifth Day of July, 2006

JON W. DUDAS
*Director of the United States Patent and Trademark Office*